United States Patent
Anyanwu et al.

(10) Patent No.: US 7,851,548 B2
(45) Date of Patent: Dec. 14, 2010

(54) LOW VISCOSITY, HIGH MOLECULAR WEIGHT LINEAR RANDOM-BLOCK SILICONE POLYALKYLENEOXIDE COPOLYMERS

(75) Inventors: Uche Kelechi Anyanwu, Hastings-on-Hudson, NY (US); Sigfredo González, Danbury, CT (US)

(73) Assignee: Momentive Performance Materials Inc., Albany, NY (US)

( * ) Notice: Subject to any disclaimer, the term of this patent is extended or adjusted under 35 U.S.C. 154(b) by 258 days.

(21) Appl. No.: 12/150,820

(22) Filed: May 1, 2008

(65) Prior Publication Data
US 2009/0274643 A1 Nov. 5, 2009

(51) Int. Cl.
*C08L 83/00* (2006.01)

(52) U.S. Cl. ............................ 524/588; 528/27; 528/28; 525/476

(58) Field of Classification Search ............... 424/78.17; 524/588; 528/10–45
See application file for complete search history.

(56) References Cited

U.S. PATENT DOCUMENTS

| 4,101,272 | A | 7/1978 | Guise et al. |
| 4,242,466 | A | 12/1980 | Schilling et al. |
| 4,833,225 | A | 5/1989 | Schaefer et al. |
| 5,130,344 | A * | 7/1992 | Kollmeier et al. ............ 521/111 |
| 5,807,956 | A | 9/1998 | Czech |
| 5,981,681 | A | 11/1999 | Czech |
| 6,475,568 | B1 | 11/2002 | Czech |
| 6,835,419 | B2 | 12/2004 | Herzig et al. |
| 2003/0022982 | A1 | 1/2003 | Yu et al. |

* cited by examiner

*Primary Examiner*—Vasu Jagannathan
*Assistant Examiner*—Doris L Lee
(74) *Attorney, Agent, or Firm*—Dominick G. Vicari (57) ABSTRACT

The present invention describes novel non-hydrolyzable, linear, random block copolymers comprising units of polysiloxanes and polyalkyleneoxides linked by bis-aminofunctional groups. These copolymers have been successfully applied as textile enhancers as well as conditioning agents for hair and skin care products.

34 Claims, 2 Drawing Sheets

LOW VISCOSITY, HIGH MOLECULAR WEIGHT LINEAR RANDOM-BLOCK SILICONE POLYALKYLENEOXIDE COPOLYMERS

FIELD OF THE INVENTION

The invention describes novel non-hydrolyzable, linear, random block copolymers comprising units of polysiloxanes and polyalkyleneoxides linked by a bis-aminofunctional group. These copolymers have been successfully applied as textile enhancers as well as conditioning agents for hair and skin care products.

DESCRIPTION OF RELATED ART

Non-hydrolyzable aminosilicone-polyalkyleneoxide block copolymers are known in the prior art. For example, U.S. Pat. No. 4,101,272 to Guise et al. discloses a process for the treatment of fibrous material to improve it properties. The process includes treating the fibrous materials with a composition consisting of epoxy-substituted polyorganosiloxanes, polyamines consisting of one or more organic compounds each with two or more primary and/or secondary amino groups attached to aliphatic carbon atoms such that they are capable of reacting in situ. U.S. Pat. No. 4,242,466 to Schilling et al. discloses organic ethers including polyethers having two $CH_2=C(R)CH_2-$ end groups per molecule, where R is a monovalent hydrocarbon, and which is reacted with an organohydrosiloxane under hydrosilation reaction conditions in the presence of platinum catalyst to form non-hydrolyzable linear block copolymers.

U.S. Pat. Nos. 5,807,956 and 5,981,681 disclose non-hydrolyzable block copolymers of the $(AB)_n$ type, comprising alternating units of polysiloxanes and amino-polyalkyleneoxides, and also describe their methods of preparation. The use of these copolymers as durable, hydrophilic textile softeners, which improve the tactile properties of the substrates, is also described therein.

U.S. Pat. No. 6,835,419 to Herzig et al. describes ammonio-containing organosilicone compounds, which are un-crosslinked, i.e. soluble in diethylene glycol and monobutyl ether, and which can be prepared by a simple process without the use of large amounts of organic solvents. Polyamines are reacted with organosilicone compounds to form a toluene-soluble amino-functional intermediate, which is subsequently protonated to form uncrosslinked solvent-soluble ammonium groups.

U.S. Pat. No. 6,475,568 to Czech discloses block non-$(AB)_n$ linear copolymers comprising units of polysiloxanes and polyalkyleneoxide linked by tertiary amino groups, a method for the preparation of these copolymers and their use as conditioning ingredients in hair care and skin care products as well as textile softeners.

It is known within the industry that high molecular weight non-hydrolyzable linear random block aminosilicone-polyalkyleneoxide copolymers can improve tactile properties of treated fiber and textile substrates. However, the existing high molecular weight copolymers of this type are impractical due to their increased viscosities, which presents issues with the handling and formulation of these copolymers as textile enhancers and conditioning agents for hair care and skin care.

The present inventors have discovered high molecular weight, easy to handle, low viscosity aminosilicone-polyalkyleneoxide copolymers with improved physical properties as described herein.

SUMMARY OF THE INVENTION

The present invention provides a non-hydrolyzable, random blocked polysiloxane-polyalkylene oxide composition having the Formula (1):

$$E^1[A]_m[B]_nE^2, \qquad (1)$$

wherein each A is independently a polysiloxane unit of structure

$-CR^1R^2-CR^3(OH)R^5-(SiR^4{}_2O)_x-SiR^4{}_2-R^5CR^3(OH)CR^1R^2-L-$ wherein each $R^1$ is selected independently from the group consisting of a hydrogen, and an alkyl, aryl, alkenyl, and aralkyl containing from 1 to 20 carbon atoms and optionally contains an oxygen atom; each $R^2$ is selected independently from the group consisting of a hydrogen, a chemical bond between the carbon atom and a different carbon atom of $R^3$ to form a ring structure, an alkyl, aryl, alkenyl, and aralkyl containing from 1 to 20 carbon atoms and optionally contains an oxygen atom; each $R^3$ is selected independently from the group consisting of a hydrogen, an alkyl, aryl, alkenyl, and aralkyl containing from 1 to 20 carbon atoms and optionally contains an oxygen atom, with the proviso that if $R^2$ is a chemical bond, then $R^3$ is a divalent hydrocarbon of 1 to 20 carbon atoms an optionally contains an oxygen atom that form a ring containing the chemical bond, $R^2$; each $R^4$ is independently selected from the group consisting of hydrogen, and an alkyl, alkenyl, aryl or aralkyl group containing 1 to 10 carbon atoms; each $R^5$ is a divalent hydrocarbon radical containing from 1 to 20 carbon atoms and optionally containing an oxygen atom; each L is independently a divalent linking group selected from the group consisting of $-N(R^6NR^7{}_2)-$, and wherein each $R^6$ is a divalent hydrocarbon radical containing from 1 to 20 carbon atom, each $R^7$ is an independently monovalent hydrocarbon radical containing from 1 to 20 carbon atoms and $R^8$ is a divalent hydrocarbon of containing 2 to 20 carbon atoms and optionally contains an oxygen atom or an $-NR^7-$ group; and x is an integer from 1 to 500;

each B is independently a polyalkylene oxide unit of structure $-CR^1R^2-CR^3(OH)R^5-O(C_aH_{2a}O)_bR^5CR^3(OH)CR^1R^2-L-$ wherein each $R^1$ is selected independently from the group consisting of a hydrogen, and an alkyl, aryl, alkenyl, and aralkyl containing from 1 to 20 carbon atoms and optionally contain a oxygen atom; each $R^2$ is selected independently from the group consisting of a hydrogen, a chemical bond between the carbon atom and a different carbon atom of $R^3$ to form a ring structure, an alkyl, aryl, alkenyl, and aralkyl containing from 1 to 20 carbon atoms and optionally contain a oxygen atom; each $R^3$ is selected independently from the group consisting of a hydrogen, an alkyl, aryl, alkenyl, and aralkyl containing from 1 to 20 carbon atoms and optionally contain a oxygen atom, with the proviso that if $R^2$ is a chemical bond, then $R^3$ is a divalent hydrocarbon of 1 to 20 carbon atoms an optionally contains an oxygen atom that form a ring containing the chemical bond, $R^2$; each $R^5$ is a divalent hydrocarbon radical containing from 1 to 20 carbon atoms and optionally containing an oxygen atom; each L is independently a divalent linking group selected from the group consisting of wherein each $R^6$ is a divalent hydrocarbon radical containing from 1 to 20 carbon atom, each $R^7$ is an independently monovalent hydrocarbon radical containing from 1 to 20 carbon atoms and $R^8$ is a divalent hydrocarbon of containing 2 to 20 carbon atoms and optionally contains an oxygen atom or an —$NR^7$— group; and x is an integer from 1 to 500;

each $E^1$ is a monovalent end-group independently selected from the group consisting of, and H-L; and each $E^2$ is a monovalent end-group independently selected from the group consisting of hydrogen, each m and n is independently an integer from 1 to 500, and a is from 2 to 4, b is from 2 to 100, and preferably 3 to 50.

The present invention further provides a method of making a non-hydrolyzable, random blocked polysiloxane-polyalkylene oxide composition having the Formula (1):

wherein each A is independently a polysiloxane unit of structure

—$CR^1R^2$—$CR^3(OH)R^5$—$(SiR^4{}_2O)_x$—$SiR^4{}_2$—$R^5CR^3(OH)CR^1R^2$-L- wherein each $R^1$ is selected independently from the group consisting of a hydrogen, and an alkyl, aryl, alkenyl, and aralkyl containing from 1 to 20 carbon atoms and optionally contains an oxygen atom; each $R^2$ is selected independently from the group consisting of a hydrogen, a chemical bond between the carbon atom and a different carbon atom of $R^3$ to form a ring structure, an alkyl, aryl, alkenyl, and aralkyl containing from 1 to 20 carbon atoms and optionally contains an oxygen atom; each $R^3$ is selected independently from the group consisting of a hydrogen, an alkyl, aryl, alkenyl, and aralkyl containing from 1 to 20 carbon atoms and optionally contains an oxygen atom, with the proviso that if $R^2$ is a chemical bond, then $R^3$ is a divalent hydrocarbon of 1 to 20 carbon atoms an optionally contains an oxygen atom that form a ring containing the chemical bond, $R^2$; each $R^4$ is independently selected from the group consisting of hydrogen, and an alkyl, alkenyl, aryl or aralkyl group containing 1 to 10 carbon atoms; each $R^5$ is a divalent hydrocarbon radical containing from 1 to 20 carbon atoms and optionally containing an oxygen atom; each L is independently a divalent linking group selected from the group consisting of wherein each $R^6$ is a divalent hydrocarbon radical containing from 1 to 20 carbon atom, each $R^7$ is an independently monovalent hydrocarbon radical containing from 1 to 20 carbon atoms and $R^8$ is a divalent hydrocarbon of containing 2 to 20 carbon atoms and optionally contains an oxygen atom or an —$NR^7$— group; and x is an integer from 1 to 500;

each B is independently a polyalkylene oxide unit of structure

—$CR^1R^2$—$CR^3(OH)R^5$—$O(C_aH_{2a}O)_b R^5CR^3(OH)CR^1R^2$-L- wherein each $R^1$ is selected independently from the group consisting of a hydrogen, and an alkyl, aryl, alkenyl, and aralkyl containing from 1 to 20 carbon atoms and optionally contain a oxygen atom; each $R^2$ is selected independently from the group consisting of a hydrogen, a chemical bond between the carbon atom and a different carbon atom of $R^3$ to form a ring structure, an alkyl, aryl, alkenyl, and aralkyl containing from 1 to 20 carbon atoms and optionally contain a oxygen atom; each $R^3$ is selected independently from the group consisting of a hydrogen, an alkyl, aryl, alkenyl, and aralkyl containing from 1 to 20 carbon atoms and optionally contain a oxygen atom, with the proviso that if $R^2$ is a chemical bond, then $R^3$ is a divalent hydrocarbon of 1 to 20 carbon atoms an optionally contains an oxygen atom that form a ring containing the chemical bond, $R^2$; each $R^5$ is a divalent hydrocarbon radical containing from 1 to 20 carbon atoms and optionally containing an oxygen atom; each L is independently a divalent linking group selected from the group consisting of wherein each $R^6$ is a divalent hydrocarbon radical containing from 1 to 20 carbon atom, each $R^7$ is an independently monovalent hydrocarbon radical containing from 1 to 20 carbon atoms and $R^8$ is a divalent hydrocarbon of containing

2 to 20 carbon atoms and optionally contains an oxygen atom or an —NR$^7$— group; and x is an integer from 1 to 500;

each E$^1$ is a monovalent end-group independently selected from the group consisting of, and H-L-; and each E$^2$ is a monovalent end-group independently selected from the group consisting of hydrogen, each m and n are independently an integer from 1 to 500, and a is an integer from 2 to 4, b is an integer from 2 to 100, and preferably 3 to 50, wherein the method comprises reacting i) polysiloxane A, and ii) polyalkylene oxide B, with at least one E$^1$ monovalent end-group and at least one E$^2$ monovalent end-group.

The presently disclosed non-hydrolyzable, random block polysiloxane, polyalkyleneoxide copolymer linked by a bis-aminofunctional group, which on one end forms a tertiary amine linkage between the monomers within the polymer chain and the other end resides as a pendant amino-functional group, provides high molecular weight copolymers with low and manageable viscosities. The presently claimed copolymer can be handled and formulated easily when formulating emulsions. These high molecular weight copolymers enhance the tactile properties of textile substrates and improve the conditioning ingredients in hair care and skin care products.

DESCRIPTION OF THE PREFERRED EMBODIMENTS

The singular forms "a," "an" and "the" include plural referents unless the context clearly dictates otherwise. The endpoints of all ranges reciting the same characteristic are independently combinable and inclusive of the recited endpoint. All references are incorporated herein by reference.

The modifier "about" used in connection with a quantity is inclusive of the stated value and has the meaning dictated by the context (e.g., includes the tolerance ranges associated with measurement of the particular quantity).

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

In each generic structural chemical formula described and/or claimed herein wherein two or more substituents (inclusive of such terms as "groups," "functional groups," "radicals" and "moieties") are each defined as any one of several specified members, the structural formula shall be regarded as including all possible combinations of members defining all such substituents (subgenuses) and as disclosing each combination (subgenus) as if it were individually set forth.

The present invention discloses non-hydrolyzable, linear, random-block copolymers comprising units of polydimethylsiloxanes and polyalkyleneoxides linked by tertiary amino groups. Inventively, the linking units of the copolymer comprise two tertiary amino groups, or a tertiary and a secondary amino group, wherein the tertiary amine resides within the polymer's backbone chain, linking the monomer units together, and the other secondary or tertiary amine (i.e., amino-functional group(s)) consequently exists as a residual pendant group.

Furthermore, the present invention provides a method for the preparation of the random-block copolymer by the addition of equimolar amounts of an epoxy end-blocked silicone and an epoxy end-blocked polyalkyleneoxide to a mixture of an amine, which serves as a linker, in a solvent, e.g., isopropanol. Polymerization of the copolymer is facilitated by amine ring-opening reactions with both epoxy end-blocked silicone and polyether moieties. This effectively results in a random block copolymer in which the component oligomeric monomers are linked together by tertiary amine groups.

The degree of polymerization, which dictates the chain length and consequently the molecular weight, is directly related to the molar ratio of the amine linking group to the epoxy end-blocked monomers. A molar excess of amine is typically used to modulate the degree of polymerization. The inventors have discovered that variations of this molar ratio do not significantly affect the viscosity of the copolymer composition when bis-amino functional linking groups are used to prepare the copolymer. For example, a 23 and 8 percent molar excess amine of diethylaminopropylamine (DEAPA) yields a product having a 3,000 cPs and 7,000 cPs, respectively. In sharp contrast, the use of monoethanolamine in a 23 and 8 percent molar excess amine yields copolymers of 25,000-30,000 cPs and 100,000-105,000 cPs, respectively. As noted, the viscosity of the copolymer is significantly influenced by the amount of amine used. As such, high molecular weight copolymers may be achieved with little consequence in viscosity. Reduced viscosity is obtained through the absence of H-bonding association with pendant hydroxyl groups when hydroxyl amino functional linking groups are used. (e.g., ethanolamine). Thus, allowing for relative ease in handling and formulation along with an associated improvement of softness and slickness of treated fabric.

The block copolymers of the present invention have in their structure, polysiloxane units $—CR^1R^2—CR^3(OH)R^5—(SiR^4{}_2O)_x—SiR^4{}_2—R^5CR^3(OH)CR^1R^2—$, i.e., component $[A]_m$, wherein m is an integer from 1 to 500, each $R^1$ is selected independently from the group consisting of a hydrogen, and an alkyl, aryl, alkenyl, and aralkyl containing from 1 to 20 carbon atoms and optionally contains an oxygen atom; each $R^2$ is selected independently from the group consisting of a hydrogen, a chemical bond between the carbon atom and a different carbon atom of $R^3$ to form a ring structure, an alkyl, aryl, alkenyl, and aralkyl containing from 1 to 20 carbon atoms and optionally contains an oxygen atom; each $R^3$ is selected independently from the group consisting of a hydrogen, an alkyl, aryl, alkenyl, and aralkyl containing from 1 to 20 carbon atoms and optionally contains an oxygen atom, with the proviso that if $R^2$ is a chemical bond, then $R^3$ is a divalent hydrocarbon of 1 to 20 carbon atoms an optionally contains an oxygen atom that form a ring containing the chemical bond, $R^2$; each $R^4$ is independently selected from the group consisting of hydrogen, and an alkyl, alkenyl, aryl or aralkyl group containing 1 to 10 carbon atoms, and preferably $R^4$ is a methyl group; each $R^5$ is a divalent hydrocarbon radical containing from 1 to 20 carbon atoms and optionally containing an oxygen atom and x is an integer from 1 to 500, and in another embodiment x is an integer from 10 to 200.

Further, the block copolymers of the present invention have in their structure, polyalkyleneoxide units $—CR^1R^2—CR^3(OH)R^5—O(C_aH_{2a}O)_bR^5CR^3(OH)CR^1R^2—$, i.e., component $[B]_n$, wherein n is an integer from 1 to 500, each $R^1$ is selected independently from the group consisting of a hydrogen, and an alkyl, aryl, alkenyl, and aralkyl containing from 1 to 20 carbon atoms and optionally contain a oxygen atom; each $R^2$ is selected independently from the group consisting of a hydrogen, a chemical bond between the carbon atom and a different carbon atom of $R^3$ to form a ring structure, an alkyl, aryl, alkenyl, and aralkyl containing from 1 to 20 carbon atoms and optionally contain a oxygen atom; each $R^3$ is selected independently from the group consisting of a hydrogen, an alkyl, aryl, alkenyl, and aralkyl containing from 1 to 20 carbon atoms and optionally contain a oxygen atom, with the proviso that if $R^2$ is a chemical bond, then $R^3$ is a divalent hydrocarbon of 1 to 20 carbon atoms an optionally contains an oxygen atom that form a ring containing the chemical bond, $R^2$; each $R^5$ is a divalent hydrocarbon radical containing from 1 to 20 carbon atoms and optionally containing an oxygen atom and a is an integer from 2 to 4 and b is an integer from 2 to 100, and preferably b is an integer from 3 to 50.

Additionally, the block copolymers of the present invention have in their structure, divalent linking groups (i.e. component -L-), selected from the group consisting of: $—N(R^6NR^7{}_2)—$, and wherein each $R^6$ is a divalent hydrocarbon radical containing from 1 to 20 carbon atom, each $R^7$ is an independently monovalent hydrocarbon radical containing from 1 to 20 carbon atoms and $R^8$ is a divalent hydrocarbon of containing 2 to 20 carbon atoms and optionally contains an oxygen atom or an $—NR^7—$ group.

According to an embodiment of the invention, divalent linking group, -L-, is an N,N-diethylaminopropylamino group. According to another embodiment of the invention, divalent linking group, -L-, is 3-Morpholinopropylamino group.

According to an embodiment of the invention, the copolymers are end-capped (i.e., components $E^1$ and $E^2$) with one of three structures, e.g., epoxy terminated siloxane fragment, epoxy terminated polyether fragment, or the linking group (i.e., -LH). Exemplary structures of the end-capping groups are:

and H-L, wherein L, $R^1$, $R^2$, $R^3$, $R^4$, $R^5$, $R^6$ and $R^7$ are previously described herein.

According to another embodiment of the invention, the moieties comprising $R^1$, $R^3$, $R^5$, $R^6$ and $R^7$ contain from one to about twenty carbon atoms, e.g., methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, methoxy, ethoxy, propoxy, butoxy, phenyl, biphenyl, naphthyl, tolyl, xylyl, anthracyl, methoxyphenyl, isomers of the foregoing, and the like.

According to an embodiment of the invention, $R^1$ is an alkyl group having from one to four carbon atoms, $R^3$ is a hydrogen, $R^5$ is a propyloxymethyl or methoxy group, $R^6$ is a propyl group, and $R^7$ is an ethyl group.

The copolymers are not $(AB)_n$ type because blocks may consist of more than one unit, therefore the nominal length of the blocks will vary. Moreover, blocks comprising more than one unit will be interrupted with the amino groups. The number of units per molecule is limited by the ability to handle high viscosity material, since the viscosity is directly proportional to the number of units, but practically there should be at least two of each unit and may be up to 1000 units. It is preferred that the terminal groups of the copolymer be H-L (amino-) groups, as noted above.

The molecular weight of the copolymers can be modified by varying the molar ratio of the epoxy component to amino component, by varying the number of oxyalkylene units and the number of siloxy groups within the polysiloxane blocks.

The ring-opened epoxides, may be aliphatic, cycloaliphatic, and may contain aromatic rings. They also contain hydroxy groups and may contain an ether linkage. According to an embodiment, the ring-opened epoxide is chosen from the following: $—CH_2CH(OH)(CH_2)vCH(OH)CH_2—$, $—CH[CH_2OH](CH_2)vCH[CH_2OH]—$, $—CH_2CH(OH)(CH_2)vCH[CH_2OH]—$, $—(CH_2)v—OCH_2CH(OH)CH_2—$; $—(CH_2vOCH_2 CH(CH_2[OH])—$ with v=2 to 6. Alternatively, the ring-opened epoxides may be derived from the following epoxycyclohexyl alkylene groups, ω-(3,4-epoxycyclohexyl)alkylene, β-(3,4-epoxycyclohexyl)ethylene,

β-(3,4-epoxycyclohexyl)-β-methylethylene, and β-(3,4-epoxy-4-methylcyclohexyl)-β-methylethylene.

The polyoxyalkylene blocks represented by $(C_aH_{2a}O)$ or $(OC_aH_{2a})$ may be made up of ethylene oxide, wherein a equals 2, propylene oxide, wherein a equals 3, and butylene oxide, wherein a equals 4 in a random or blocked fashion. The ratio among such oxides is not of particular importance, but may be adjusted as required for the desired solubility parameters of the resulting copolymer.

Method of Manufacture

The compounds of the present invention are prepared by reacting polysiloxanes and polyalkylene oxides, which are the same as the formulae above, with a primary amine or a combination of primary and secondary amines, where the secondary amine will function as a chain stopper. These species may be manufactured by means known in the art or are commercially available.

For example, α,ω-hydrogenpolysiloxanes of the general formula $H(SiO(R^1)_2)_xSi(R^1)_2H$ are reacted in a first step with the unsaturated epoxides with a terminal olefinic bond, such as allyl glycidyl ether, in the presence of a hydrosilation catalyst, such as hexachloroplatinic acid, at elevated temperature, to produce epoxy end-blocked polysiloxanes. Such procedures are known in the art as indicated in U.S. Pat. No. 3,761,444 and U.K. Patent No. 1,213,779. The following are examples of suitable epoxides with terminal olefinic groups.

The epoxy end-blocked polysiloxanes and epoxy end-blocked polyalkyleneoxides are then reacted with primary amino groups or a combination of primary and secondary amino groups. Suitable epoxy end-blocked polyalkyleneoxides are represented, for example, by DER 732 and DER 736 available from Dow Chemical Co. If the boiling point of the amine is lower than the boiling point of the solvent, the reaction is conducted in a pressurized vessel. Typically, the epoxy end-blocked polysiloxanes and epoxy end-blocked polyalkyleneoxides are added to the solution of the amine in the reaction solvent.

For practical purposes, the reaction is carried out with about a 1 to about 30 percent, preferably about 1 to about 20 percent, excess of the amine-containing species. Despite using an excess of the amine used during the preparation of the copolymers whereby the majority of the end-groups can be expected to be amines, it is possible that the epoxy end group on the polysiloxane can undergo side reactions with the solvent, water, or alcohol to form the corresponding diol or ether alcohol.

Quaternary amine analogs of copolymers of the present invention may also be achieved by quaternization reactions of the amino groups in the copolymer. Common quaternizing agents that may be used include, but are not limited to, alkyl, aryl, arylalkyl halides, sulfates or halo-substituted esters. The resulting quaternary ammonium salts may offer improved deposition properties or static electricity control as compared to the starting copolymer. An alternative way to produce quaternized structures is to react the epoxy end-blocked polysiloxanes and epoxy end-blocked polyalkyleneoxides with secondary amines, for example, N,N,N'-trimethyl-1,3-propanediamine, N,N,N',N'-Tetraethyldiethylenetriamine, N,1-dimethyl-4-piperidinamine, and the like, in the presence of a stoichiometric amount of a Bronsted acid such as hydrochloric acid, sulfuric acid or acetic acid. The reaction is carried out in a suitable solvent such as an alcohol or a mixture of alcohol and water at reflux.

Copolymer Uses

The copolymers of the present invention are primarily intended as softeners for substrates especially hair, fibers and textiles. While the copolymers of the present invention can be used neat, for ease of application they are typically applied to the substrates dissolved, dispersed or emulsified in a suitable liquid medium. According to an embodiment of the invention, the copolymers of the present invention are applied to a substrate from an aqueous solution, suspension or emulsion. They may be applied as a solution in a non-aqueous solvent such as isopropanol or a liquid in which the copolymer is miscible. In yet another embodiment, the copolymer is applied to the substrate as an aqueous micro emulsion.

Aqueous emulsions of the copolymers of the present invention may be prepared by combining the copolymer with one or more emulsifiers, including, but not limited to, nonionic surfactants, ionic surfactants and diluents. Stable aqueous dispersions of the copolymers may be, for example, prepared by directly mixing an aqueous solution of the copolymer with a water miscible solvent, such as isopropanol, propylene glycol, dipropylene glycol and dipropylene glycol methyl ether.

Prepared solutions, dispersions or emulsions may be applied onto the substrates by spraying, dipping, kiss roll, pad bath applications or other methods typically employed in fiber, hair or textile treatment. Examples of substrates that can be treated with the copolymers of the present invention include natural fibers such as hair, cotton, silk, flax, cellulose, paper (including tissue paper) and wool; synthetic fibers such as polyester, polyamide, polyacrylonitrile, polyethylene, polypropylene, polyurethane; and inorganic fibers such as carbon fibers. The fabric substrates, which can be treated with the copolymers of the present invention, include fabric produced from the above-mentioned fibrous materials of blends thereof.

In general, the solution, dispersion of emulsion of the copolymers of the present invention maybe applied of hair, fiber or textile substrates, such that up to 5%, preferably 0.2 to 2.5% of the copolymer by weight of the dry substrate remains on the substrate. Optionally, other additives commonly used to treat hair or textile substrates can be employed along with the copolymers of the present invention, including, but not limited to, additional surfactants, deposition polymers, quaternary conditioning agents, curing agents, curing resins, preservatives, dyes, colorants, optical brighteners and formularies. Moreover, compositions including copolymers of the present invention may be used in personal care formulations, including, but not limited to, cleansers, body washes, soaps, lotions, creams, shaving cream, hair sprays, conditioners, shampoos, deodorants, moisturizer and sun-blocks.

The copolymers of the present invention may be formulated into these or other products together with one or more anionic surfactants, one of more amphoteric surfactants, one or more nonionic surfactants, and/or one or more deposition polymers or thickeners. Suitable anionic surfactants include sulfonated and sulfated alkyl, arylalkyl and alkylaryl anionic compounds; alkyl succinates; alkyl sulfosuccinates; and N-alkanoyl sarcosinates. Preferred are the sodium, magnesium, ammonium and mono-, di- and triethanolamine salts of alkylaryl sulfonates. The alkyl groups preferably contain 8 to 22 carbon atoms. Sulfate ethers containing preferably 1 to 10 ethylene oxide and/or propylene oxide units may be considered.

Examples of anionic surfactants with which the copolymers of the present invention may be formulated include, but are not limited to, sodium lauryl sulfate, sodium lauryl ether sulfate, ammonium lauryl sulfate, triethanolamine lauryl sulfate, sodium $C_{14-16}$ olefin sulfonate, ammonium pareth-25 sulfate, sodium myristyl ether sulfate, ammonium lauryl ether sulfate, disodium monooleamido-sulfosuccinate, ammonium lauryl sulfosuccinate, sodium dodecylbenzene sulfonate, triethanolamine dodecylbenzene sulfonate and sodium N-lauroyl sarcosinate.

Examples of amphoteric surfactants with which the copolymers of the present invention can be formulated include cocoamphocarboxyglycinate, cocoamphocarboxypropionate, cocobetaine, N-cocoamidopropylydimethylglycine, and N-lauryl-N'-carboxymethyl-N'-(20hydroxyethyl) ethylenediamine, as well as the betaine and sultaine compounds disclosed in the CTFA Dictionary as useful in personal care products.

Examples of nonionic surfactants with which the copolymers of the present invention may be formulated include, but are not limited to, fatty acid mono- and dialkanolamides in which the fatty portion preferably contain 10 to 21 carbon atoms, and amine oxides such as N-alkyl amine oxides A typical shampoo formulation contains about 3 to 30 weight percent of an anionic and/or amphoteric surfactant component, 0.1 to 10 weight percent of a nonionic surfactant component, 0.1 to 20 weight percent of one or more copolymers of the present invention, water, preferably also an effective amount of a thickener in the order of 0.1 to 5 weight percent; examples of thickeners include sodium alginate, Arabic gum, polyoxyethylene, guar gum, hydroxypropyl guar gum, cellulosics such as methyl cellulose, methylhydroxypropyl cellulose and hydroxypropyl cellulose, starch derivatives such as hydroxyethylamylose, locust bean gum and polysaccharides.

The advantages and the important features of the present invention will be more apparent from the following examples.

Preparation of the Copolymers of the Present Invention:

Example 1 copolymer was prepared as follows: First, silanic fluid (M'D$_{50}$ M') was prepared as follows: to a two-liter, three-necked flask fitted with a mechanical stirrer and a nitrogen inlet was charged with 34.96 g of tetramethyldisiloxane and 965.0 g of the cyclic tetramer, octamethylcyclotetrasiloxane. The flask was flushed with nitrogen and 15 g of concentrated sulfuric acid was added. The flask contents were stirred at room temperature under nitrogen for approximately 24 hours. The reaction mixture was then neutralized with wet sodium bicarbonate and filtered to afford the silanic fluid as a clear, colorless fluid with a viscosity of 48 cPs and hydrogen content of 11.7 cCH$_2$/g.

Second, the preparation of epoxy end-blocked silicone (M*D$_{50}$ M*) was as follows: to a 1000 ml four-necked flask fitted with a mechanical stirrer, a condenser fitted with a nitrogen inlet, a thermometer and an addition funnel was charged with 500 g of the silanic fluid (M'D$_{50}$M') and 31.2 g of allyl glycidyl ether, AGE (5% molar excess, commercially available from Sigma-Aldrich) was placed in the addition funnel. The flask contents were heated with stirring to 80° C., was catalyzed with 3 ppm of Pt and AGE was added slowly at the temperature<90° C. After the addition was complete, stirring at 85-90° C. continued for 1 hour. Sampling after 1 hour showed no residual SiH. The reaction mixture was cooled to room temperature, neutralized with of wet sodium bicarbonate and vacuum sparge at 100°-120° C. The resulting epoxy fluid had a viscosity of 65 cPs, refractive index of 1.4070 at 25° C., and the epoxide content, as determined by a reactive titration with perchloric acid, of 1.9%.

Finally, preparation of the copolymers of Example 1 was as follows: to a 500 mL four-necked round-bottomed flask fitted with a mechanical stirrer, a condenser fitted with a nitrogen inlet, a thermocouple and an addition funnel was charged with 14.35 g of N,N-diethylaminopropylamine, DEAPA (0.1102 mol NH$_2$, 8% molar excess with respect to total moles of epoxy), 100 g of the epoxy end-blocked silicone, M*D$_{50}$M* (½ of the total charge, 0.1020 mol, 0.51 meq/g epoxy), where M* is modified with a glycidyloxypropyl group, 82 g of isopropanol (IPA) and 100 ppm of Vitamin E. The contents of the flask were heated, with stirring, to 80° C. for 2 hours after which 16.04 g (½ of the total charge, 0.1020 mol, 3.18 meq/g epoxy) of the epoxy end-blocked polyalkyleneoxide (DER 732, commercially available from Dow Chemical) was added to the flask. After 2 hours of heating, the remaining 100 g of M*D$_{50}$M* was added to the flask and the reaction mixture was heated to 80° C. for another 2 hours, followed by the final addition of the remaining 16.04 g of DER 732. The reaction mixture was maintained at 80° C., under a nitrogen blanket, until all the epoxy groups were reacted. This typically required about 6 to 10 hours. The reaction was deemed complete when identical numbers were obtained from the epoxy titration and amine titration of the product. The contents of the flask were then transferred to a 1000 mL round bottomed recovery flask, placed on a rotary evaporator, and heated at 130° C. in an oil bath. The solvent was stripped under reduced pressure (~2 torr) for 2 h to afford a clear, straw colored fluid with IPA content of <1%, a viscosity of 7,400 cPs and total amine content of 0.90 meq/g. The viscosity was measured with a Brookfield viscometer, spindle #4, at 25° C.

Example 2 copolymer was prepared as a quaternary ammonium salt of Example 1 copolymer as follows: Quaternization of the amine groups in Example 1 was achieved by reacting the copolymer with methylchlorocacetate (>99%, commercially available from Sigma-Aldrich). 25.07 g of methylchloroacetate (0.224 mol, 2% molar excess with respect to total molar amine content of copolymer Example 1) is added to the reaction mixture. The reaction is allowed to continue, under reflux, for an additional hour to ensure that all amine groups are quaternized, and a viscosity increase is observed. Excess methylchloroacetate is removed by rotary evaporation to yield a viscous pale yellow fluid.

Secondary (non-covalent) intermolecular interactions often times play a significant role in influencing the rheological properties of polymers. This effect was observed when representative copolymers were prepared using the following amine linking groups: (1) Monoethanolamine (MEA), (2) Diethylaminopropylamine (DEAPA) and (3) 3-Morpholinopropylamine (MPA). Examples 7-14 and Comparative Examples 3-6 were prepared by the same method used in Example 1 using 23%, 18%, 13% and 8% excess amine. The viscosities of the products were measured at 25° C. and reported below in Table 1.

TABLE 1

Viscosities of copolymers prepared with varying molar excess amine

| Amine | % Excess Amine | Viscosity (cPs) |
|---|---|---|
| H$_2$N$\diagup\!\!\diagdown$OH (MEA) | 8 (Comp. Example 3) | 103400 |
|  | 13 (Comp. Example 4) | 50000 |
|  | 18 (Comp Example 5) | 35000 |
|  | 23 (Comp. Example 6) | 30900 |
| H$_2$N$\diagup\!\!\diagdown$N(Et)$_2$ (DEAPA) | 8 (Example 7) | 7400 |
|  | 13 (Example 8) | 4600 |
|  | 18 (Example 9) | 4000 |
|  | 23 (Example 10) | 3665 |
| H$_2$N$\diagup\!\!\diagdown$N-morpholino (MPA) | 8 (Example 11) | 30000 |
|  | 13 (Example 12) | 22000 |
|  | 18 (Example 13) | 12200 |
|  | 23 (Example 14) | 10350 |

Increasing the amount of amine used in each case, from 8% to 23% excess amine, yields copolymers with correspondingly lower viscosities. However, this effect is noticeably less significant in the case of the present invention, where DEAPA is used.

Figure 1:
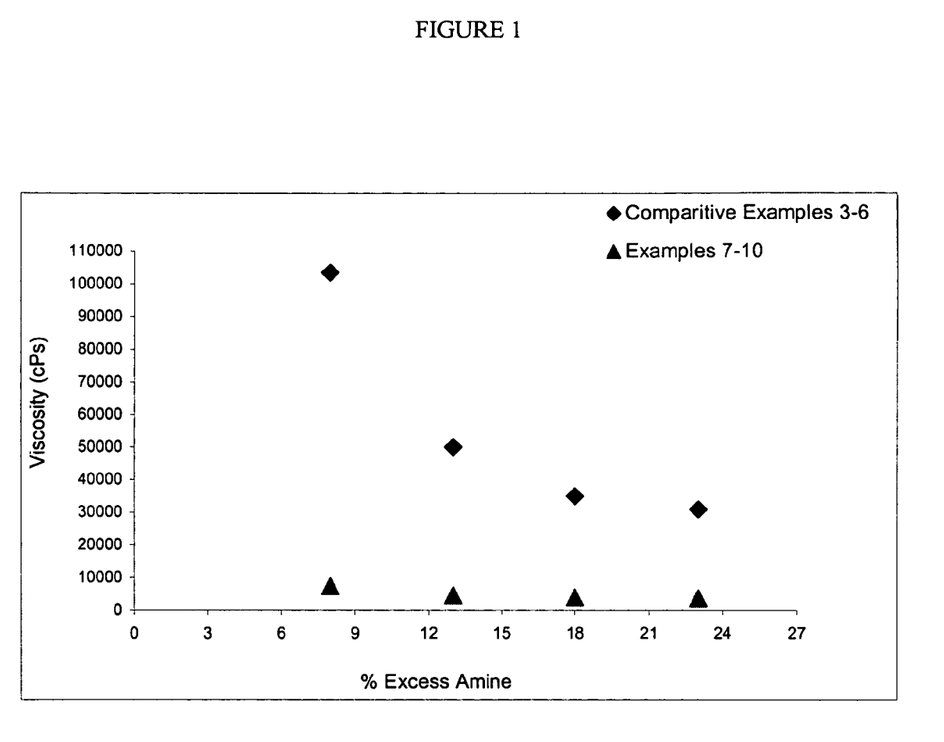
FIG. 1 is a graphical representation of viscosity verses percent (%) excess amine of copolymers prepared using diethylaminopropylamine (i.e., Examples 7-10 of the invention) and monoethanolamine (i.e., Comparative Examples 3-6).

FIG. 1 is a graphical representation of viscosity verses percent (%) excess amine of copolymers of Examples 7-10 and Comparative Examples 3-6 that were prepared using DEAPA and MEA, respectively.

A key feature and benefit of the present invention is the ability to achieve high molecular weight copolymers with little consequence in viscosity. This circumvents issues associated with handling and formulation of typically high molecular weight, high viscosity copolymers. The relationship between viscosity of the copolymers of Examples 7-10 and Comparative Examples 3-6 and their respective molar % excess amine and molecular weight is presented in FIGS. 1 and 2.

Figure 2:
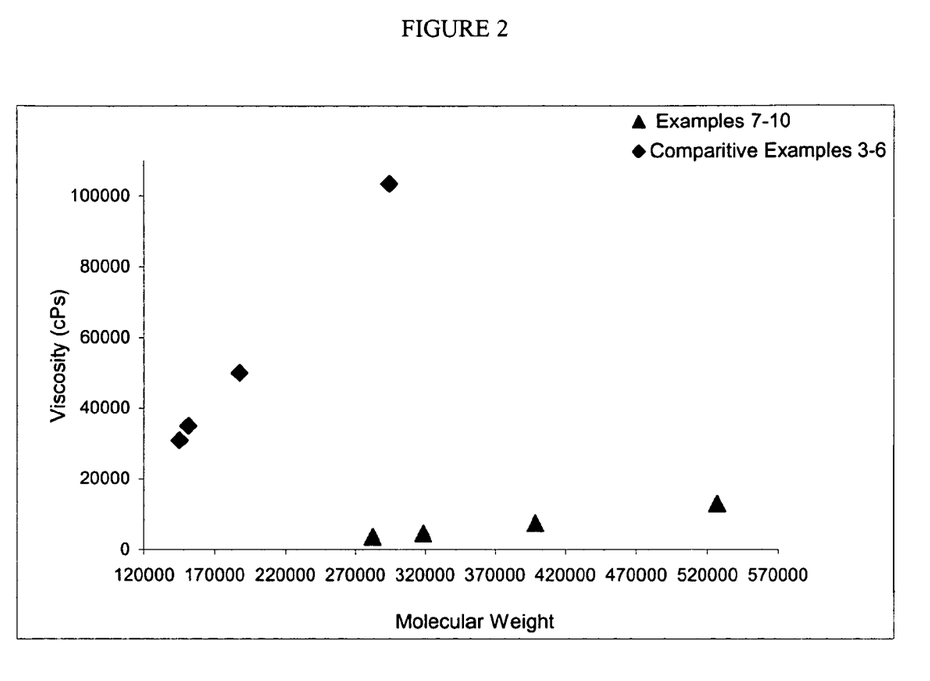
FIG. 2 is a graphical representation of viscosity verses molecular weight of copolymers prepared using diethylaminopropylamine (i.e., Examples 7-10 of the invention) and monoethanolamine (i.e., Comparative Examples 3-6).

FIG. 2 is a graphical representation of viscosity verses molecular weight of copolymers of Examples 7-10 and Comparative Examples 3-6 that were prepared using DEAPA and MEA, respectively.

The following Examples were prepared using selected copolymers of the present invention, as microemulsions in water, and used for testing performance on the hand properties (i.e., softness and slickness) of textiles.

Example 15 is a microemulsion prepared from an emulsion concentrate comprising: TDA-10 surfactant (Ethox Chemical LLC), 11%, Tergitol 15-S-15, 2.8%, Butylcarbitol, 9%, Emulsogen, 5%, water, 5.7% and the copolymer of Example 1 (prepared with 8% molar excess amine) 66.5%.

Example 16 is a microemulsion prepared from an emulsion concentrate comprising: TDA-10 surfactant (Ethox Chemical LLC), 11%, Tergitol 15-S-15 (Dow Chemical Co.), 2.8%, Butylcarbitol (Dow Chemical Co.), 9%, Emulsogen (Clarient), 5%, water, 5.7% and a copolymer prepared following the same procedure as that used for the copolymer of Example 1, however, with a stoichiometric amount of amine (0% molar excess amine), 66.5%.

Example 17 is a microemulsion prepared from an emulsion concentrate comprising: TDA-6 surfactant (Ethox Chemical LLC), 10.5%, TDA-12 surfactant (Ethox Chemical LLC), 1.8%, Glacial Acetic Acid (Fisher Chemicals), 0.4%, Sodium Acetate (Fisher Chemicals), 0.3%, Deionized Water, 67% and Example 2, the quaternary amine analog of Example 1 (where 100% of the amine groups in the polymer are quaternized with methylchloroacetate), 20%.

Comparative Example 7 (Magnasoft JSS®, a commercial textile enhancer from Momentive Performance Materials, Tarrytown, N.Y.) is a microemulsion prepared from an emulsion concentrate comprising: TDA-10 surfactant (Ethox Chemical LLC), 11%, Tergitol 15-S-15, 2.8%, Butylcarbitol, 9%, Emulsogen, 5%, water, 4.7%, 20% (w/w) aqueous solution of sodium hydroxide (Fisher Scientific), 1%, and Silsoft® A-553, 66.5% (Silsoft® A-553 is a random (AB)$_n$ amino-polysiloxane-polyalkyleneoxide copolymer, prepared from reacting M*D$_{50}$M*, where M* is a glycidyloxypropyl group, with DER 732, using 23% molar excess amine).

The results are displayed in Table 3. Comparative Example 7 and Examples 15-17 are presented in Table 2, and were applied onto 100% cotton knit from a pad bath.

TABLE 2

| Textile Enhancer | Example 15 | Example 16 | Example 17 | Comparative Example 7 |
|---|---|---|---|---|
| Copolymer | Example 1 | Example 1 | Example 2 | Silsoft ® A-553 |
| Epoxysilicone | M*D$_{50}$M* | M*D$_{50}$M* | M*D$_{50}$M* | M*D$_{50}$M* |
| Epoxypolyalkyleneoxide | DER 732 | DER 732 | DER 732 | DER 732 |
| Amine | DEAPA | DEAPA | DEAPA | MEA |
| Molar Excess Amine (%) | 8 | 0 | 8 | 23 |
| Copolymer Viscosity (cPs) | 7,400 | 13,000 | >300,000 | 45,000 |

M* is glycidyloxypropyl groups.

The copolymer concentration in the treatment composition was such that the effective add-on level to the fabric was 0.5% (based on 100% wet pickup). Curing conditions were 130° C. for 5 minutes. Kawabata Evaluation System (KES) was used to measured softness and slickness of the treated fabric and the results are summarized in Table 3.

TABLE 3

Copolymer softness and slickness measured by Kawabata Evaluation System

| Textile Enhancer/ Copolymer | Softness [(B + 2HB)/2] | Slickness (Ave. MIU) |
|---|---|---|
| Comparative Example 7 | 0.0587 | 0.131 |
| Example 15 | 0.0491 | 0.140 |
| Example 16 | 0.052 | 0.131 |
| Example 17 | 0.0459 | 0.133 |

For [(B+2HB)/2] and (Ave. MIU), i.e., "softness" and "slickness", respectively, the lower the value the better the performance.

The data presented in Table 3 demonstrates that Examples 16 and 17, of the present invention, provided softness and slickness properties to the textile that were superior to Comparative Example 7 (i.e., Magnasoft JSS®/Silsoft® A-553.

Hair conditioning properties of copolymers of the present invention were tested in a side-by-side comparison, human hair was treated with SME® 253 (a pendant aminosilicone fluid commercially available from Momentive Performance Materials), Silsoft® A-553, and the silicone copolymers of Example 1 (prepared with both 0% molar excess amine and 8% molar excess amine) and Example 2. The copolymers were microemulsified prior to addition to the conditioner base. Combing force measurements were carried out to evaluate the performance of the hair after treatment with conditioning formulations. This combing force test protocol measures the percent (%) reduction of the plateau load. The plateau load is the initial force required to comb through the hair tress with a fine teeth comb. Table 4 shows the composition of the conditioner base.

TABLE 4

Conditioner base composition

| Component | Weight % |
|---|---|
| Glyceryl stearate, ceteareth-20, ceteareth-12, cetearyl alcohol and cetyl palmitate[1] | 10 |
| Silicone active (copolymer)[2] | 1.4 |
| Water | 88.6 |

[1]Trade name: Emulgade ® SE-PF from Cognis.
[2]The silicone active was microemulsified prior to addition into the conditioner base. The microemulsion contains 20% silicone active, 10% Tergitol TMN-10 (Union Carbide), 3% glycerin and water. The pH was adjusted to 4 with acetic acid.

Hair Tress Preparation:

Virgin European black hair and double bleached blond hair (4 g tresses, 15 cm long) were purchased from Hair International Inc. Prior to washing, each tress was dipped into 0.5% aqueous sodium hydroxide solution for two minutes and subsequently rinsed for two minutes with tap water. Each tress was then washed with 1 ml of a 10% SLES solution and rinsed using a standard wash protocol. After washing, the wet tresses were combed with a fine teeth comb, dried in a blow drier bonnet and kept overnight in a environmental chamber at 50% relative humidity before combing force measurements. These clean tresses were used to measure the baseline combing force, according to the combing force protocol described below. After the baseline measurement, the tresses were washed again with the SLES (sodium lauryl ethyl sulfate) solution and treated with a conditioner (1 ml/tress) as described below. After rinsing, drying and combing, the treated tresses were kept overnight in an environmental chamber at 50% relative humidity before combing force measurements were performed.

Dry Combing Force Measurement:

The combing force measurements were performed on a Diastron combing force apparatus, which was enclosed in a controlled humidity chamber, equilibrated at 50% relative humidity. The automated comb speed was 500 mm/min. The combing force measurements were carried out on virgin hair and damaged hair. Measurements were repeated 10 times on each tress and each treatment was duplicated. The results are summarized in Table 5 and Table 6 below.

TABLE 5

Combing force data obtained on virgin hair

| | | Untreated | | Treated | | |
|---|---|---|---|---|---|---|
| Treatment (Conditioner base) | Swatch # | Average Plateau Load (g) | Std. Dev. | Average Plateau Load (g) | Std. Dev. | Reduction (%) |
| Comparative Example 8 (control- contained no silicone) | 1 | 10.07 | 1.23 | 9.33 | 0.77 | 4.74 |
| | 2 | 10.59 | 2.76 | 10.37 | 1.75 | |
| SME ® 253 | 1 | 6.67 | 1.39 | 5.68 | 0.79 | 13.93 |
| | 2 | 13.26 | 1.75 | 11.53 | 2.81 | |
| Silsoft ® A553 | 1 | 8.29 | 1.18 | 6.73 | 0.59 | 20.53 |
| | 2 | 5.305 | 0.97 | 4.13 | 0.60 | |

TABLE 5-continued

Combing force data obtained on virgin hair

| | | Untreated | | Treated | | |
|---|---|---|---|---|---|---|
| Treatment (Conditioner base) | Swatch # | Average Plateau Load (g) | Std. Dev. | Average Plateau Load (g) | Std. Dev. | Reduction (%) |
| Example 2 | 1 | 5.30 | 1.10 | 3.48 | 0.73 | 34.17 |
| | 2 | 6.01 | 1.19 | 3.97 | 0.42 | |
| Example 1(0% molar excess amine) | 1 | 5.97 | 1.34 | 3.39 | 0.82 | 44.00 |
| | 2 | 7.75 | 0.88 | 4.29 | 0.58 | |
| Example 1(8% molar excess amine) | 1 | 20.06 | 3.21 | 10.54 | 2.99 | 58.33 |
| | 2 | 10.25 | 2.51 | 3.16 | 0.47 | |

TABLE 6

Combing force data obtained on damaged hair

| | | Untreated | | Treated | | |
|---|---|---|---|---|---|---|
| Treatment (Conditioner base) | Swatch # | Average Plateau Load (g) | Std. Dev. | Average Plateau Load (g) | Std. Dev. | % Reduction |
| Comparative Example 8 (control- contained no silicone) | 1 | 40.51 | 6.20 | 54.23 | 7.05 | −8.88 |
| | 2 | 40.75 | 6.24 | 34.19 | 4.77 | |
| SME ® 253 | 1 | 48.62 | 5.06 | 43.22 | 6.45 | 10.71 |
| | 2 | 40.22 | 6.70 | 36.07 | 3.49 | |
| Silsoft ® A553 | 1 | 65.97 | 12.50 | 21.14 | 4.57 | 68.40 |
| | 2 | 64.56 | 6.21 | 20.11 | 8.49 | |
| Example 2 | 1 | 45.57 | 7.23 | 16.95 | 2.01 | 65.81 |
| | 2 | 84.37 | 14.20 | 26.31 | 3.41 | |
| Example 1 (0% molar excess amine) | 1 | 61.62 | 13.67 | 16.13 | 1.78 | 67.18 |
| | 2 | 72.85 | 8.88 | 28.75 | 5.45 | |
| Example 1 (8% molar excess amine) | 1 | 45.18 | 4.83 | 15.28 | 2.47 | 66.37 |
| | 2 | 57.01 | 7.34 | 19.07 | 1.37 | |

Hair treated with the conditioning formulation containing copolymer ingredients of the present invention showed improvement in combability as observed through the marked reduction in plateau load compared to hair treated with conventional aminosilicone, SME® 253. A noticeable improvement in conditioning properties of the copolymers of the present invention, compared to random-block $(AB)_n$ copolymer Silsoft® A553, is observed in the case of virgin hair.

While the invention has been described with reference to a preferred embodiment, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

The invention claimed is:

1. A composition comprising a non-hydrolyzable, random blocked polysiloxane-polyalkylene oxide composition of the Formula (1):

$$E^1[A]_m[B]_n E^2,$$

wherein each A is independently a polysiloxane unit of structure

—CR¹R²—CR³(OH)R⁵—(SiR⁴₂O)ₓ—SiR⁴₂—R⁵CR³(OH)CR¹R²-L- wherein each $R^1$ is selected independently from the group consisting of a hydrogen, and an alkyl, aryl, alkenyl, and aralkyl containing from 1 to 20 carbon atoms and optionally contains an oxygen atom; each $R^2$ is selected independently from the group consisting of a hydrogen, a chemical bond between the carbon atom and a different carbon atom of $R^3$ to form a ring structure, an alkyl, aryl, alkenyl, and aralkyl containing from 1 to 20 carbon atoms and optionally contains an oxygen atom; each $R^3$ is selected independently from the group consisting of a hydrogen, an alkyl, aryl, alkenyl, and aralkyl containing from 1 to 20 carbon atoms and optionally contains an oxygen atom, with the proviso that if $R^2$ is a chemical bond, then $R^3$ is a divalent hydrocarbon of 1 to 20 carbon atoms an optionally contains an oxygen atom that form a ring containing the chemical bond, $R^2$; each $R^4$ is independently selected from the group consisting of hydrogen, and an alkyl, alkenyl, aryl or aralkyl group containing 1 to 10 carbon atoms; each $R^5$ is a divalent hydrocarbon radical containing from 1 to 20 carbon atoms and optionally containing an oxygen atom; each L is independently a divalent linking group selected from the group consisting of —N(R⁶NR⁷₂)—, and wherein each $R^6$ is a divalent hydrocarbon radical containing from 1 to 20 carbon atom, each $R^7$ is an independently monovalent hydrocarbon radical containing from 1 to 20 carbon atoms and $R^8$ is a divalent hydrocarbon of containing 2 to 20 carbon atoms and optionally contains an oxygen atom or an —NR⁷— group; and x is an integer from 1 to 500;

each B is independently a polyalkylene oxide unit of structure

—CR¹R²—CR³(OH)R⁵—O(CₐH₂ₐO)ᵦR⁵CR³(OH)CR¹R²-L- wherein each $R^1$ is selected independently from the group consisting of a hydrogen, and an alkyl, aryl, alkenyl, and aralkyl containing from 1 to 20 carbon atoms and optionally contain a oxygen atom; each $R^2$ is selected independently from the group consisting of a hydrogen, a chemical bond between the carbon atom and a different carbon atom of $R^3$ to form a ring structure, an alkyl, aryl, alkenyl, and aralkyl containing from 1 to 20 carbon atoms and optionally contain a oxygen atom; each $R^3$ is selected independently from the group consisting of a hydrogen, an alkyl, aryl, alkenyl, and aralkyl containing from 1 to 20 carbon atoms and optionally contain a oxygen atom, with the proviso that if $R^2$ is a chemical bond, then $R^3$ is a divalent hydrocarbon of 1 to 20 carbon atoms an optionally contains an oxygen atom that form a ring containing the chemical bond, $R^2$; each $R^5$ is a divalent hydrocarbon radical containing from 1 to 20 carbon atoms and optionally containing an oxygen atom; each L is independently a divalent linking group selected from the group consisting of —N(R⁶NR⁷₂)—, and wherein each $R^6$ is a divalent hydrocarbon radical containing from 1 to 20 carbon atom, each $R^7$ is an independently monovalent hydrocarbon radical containing from 1 to 20 carbon atoms and $R^8$ is a divalent hydrocarbon of containing 2 to 20 carbon atoms and optionally contains an oxygen atom or an —NR⁷— group; and x is an integer from 1 to 500;

each $E^1$ is a monovalent end-group independently selected from the group consisting of, and H-L-; and each $E^2$ is a monovalent end-group independently selected from the group consisting of hydrogen, each m and n is independently an integer from 1 to 500 and a is an integer from 2 to 4, b is an integer from 2 to 100.

2. The composition of claim 1 wherein b in the $E^1$ and $E^2$ end groups is an integer from 3 to 50 and x in the $E^1$ and $E^2$ end groups is an integer from 10 to 200.

3. The composition of claim 1 wherein $R^1$ is an alkyl group having from one to four carbon atoms.

4. The composition of claim 1 wherein $R^2$ is a chemical bond.

5. The composition of claim 1 wherein $R^2$ is a hydrogen.

6. The composition of claim 1 wherein $R^3$ is a hydrogen.

7. The composition of claim 1 wherein $R^4$ is a methyl group.

8. The composition of claim 1 wherein $R^5$ is a propyloxymethyl or methoxy group.

9. The composition of claim 1 wherein $R^6$ is a propyl group.

10. The composition of claim 1 wherein $R^7$ is an ethyl group.

11. The composition of claim 1 wherein -L- is at least one selected from the group consisting of N,N-diethylaminopropylamino group and 3-Morpholinopropylamino group.

12. The composition of claim 1 wherein components $E^1$ and $E^2$ are independently selected from the group consisting of —CH$_2$CH(OH)(CH$_2$)$_v$CH(OH)CH$_2$—, —CH[CH$_2$OH](CH$_2$)$_v$CH[CH$_2$OH]—, —CH$_2$CH(OH)(CH$_2$)$_v$CH[CH$_2$OH]—, —(CH$_2$)$_v$OCH$_2$CH(OH)CH$_2$—; —(CH$_2$,OCH$_2$CH(CH$_2$[OH])—, and v is an integer from 2 to 6.

13. The composition of claim 1 wherein $E^1$ and $E^2$ are independently selected from the group consisting of ω-(3,4-epoxycyclohexyl)alkylene, β-(3,4-epoxycyclohexyl)ethylene, β-(3,4-epoxycyclohexyl)-β-methylethylene, and β-(3,4-epoxy-4-methylcyclohexyl)-β-methylethylene.

14. The composition of claim 1 wherein —C$_a$H$_{2a}$O— is at least one of ethylene oxide wherein a equals 2, propylene oxide wherein a equals 3, and butylene oxide wherein a equals 4.

15. The composition of claim 1 wherein the amine groups are protonated or quaternized.

16. A personal care product comprising the composition of claim 1.

17. A textile enhancer comprising the composition of claim 1.

18. A method of making a non-hydrolyzable, random blocked polysiloxane-polyalkylene oxide composition of the Formula (1):

$E^1[A]_m[B]_nE^2$, wherein each A is independently a polysiloxane unit of structure —CR$^1$R$^2$—CR$^3$(OH)R$^5$—(SiR$^4$$_2$O)$_x$—SiR$^4$$_2$—R$^5$CR$^3$(OH)CR$^1$R$^2$-L- wherein each R$^1$ is selected independently from the group consisting of a hydrogen, and an alkyl, aryl, alkenyl, and aralkyl containing from 1 to 20 carbon atoms and optionally contains an oxygen atom; each R$^2$ is selected independently from the group consisting of a hydrogen, a chemical bond between the carbon atom and a different carbon atom of R$^3$ to form a ring structure, an alkyl, aryl, alkenyl, and aralkyl containing from 1 to 20 carbon atoms and optionally contains an oxygen atom; each R$^3$ is selected independently from the group consisting of a hydrogen, an alkyl, aryl, alkenyl, and aralkyl containing from 1 to 20 carbon atoms and optionally contains an oxygen atom, with the proviso that if R$^2$ is a chemical bond, then R$^3$ is a divalent hydrocarbon of 1 to 20 carbon atoms an optionally contains an oxygen atom that form a ring containing the chemical bond, R$^2$; each R$^4$ is independently selected from the group consisting of hydrogen, and an alkyl, alkenyl, aryl or aralkyl group containing 1 to 10 carbon atoms; each R$^5$ is a divalent hydrocarbon radical containing from 1 to 20 carbon atoms and optionally containing an oxygen atom; each L is independently a divalent linking group selected from the group consisting of —N(R$^6$NR$^7$$_2$)—, and wherein each R$^6$ is a divalent hydrocarbon radical containing from 1 to 20 carbon atom, each R$^7$ is an independently monovalent hydrocarbon radical containing from 1 to 20 carbon atoms and R$^8$ is a divalent hydrocarbon of containing 2 to 20 carbon atoms and optionally contains an oxygen atom or an —NR$^7$— group; and x is an integer from 1 to 500;

each B is independently a polyalkylene oxide unit of structure

—CR$^1$R$^2$—CR$^3$(OH)R$^5$—O(C$_a$H$_{2a}$O)$_b$R$^5$CR$^3$(OH)CR$^1$R$^2$-L- wherein each R$^1$ is selected independently from the group consisting of a hydrogen, and an alkyl, aryl, alkenyl, and aralkyl containing from 1 to 20 carbon atoms and optionally contain a oxygen atom; each R$^2$ is selected independently from the group consisting of a hydrogen, a chemical bond between the carbon atom and a different carbon atom of R$^3$ to form a ring structure, an alkyl, aryl, alkenyl, and aralkyl containing from 1 to 20 carbon atoms and optionally contain a oxygen atom; each R$^3$ is selected independently from the group consisting of a hydrogen, an alkyl, aryl, alkenyl, and aralkyl containing from 1 to 20 carbon atoms and optionally contain a oxygen atom, with the proviso that if R$^2$ is a chemical bond, then R$^3$ is a divalent hydrocarbon of 1 to 20 carbon atoms an optionally contains an oxygen atom that form a ring containing the chemical bond, R$^2$; each R$^5$ is a divalent hydrocarbon radical containing from 1 to 20 carbon atoms and optionally containing an oxygen atom; each L is independently a divalent linking group selected from the group consisting of —N(R$^6$NR$^7$$_2$)—, and wherein each R$^6$ is a divalent hydrocarbon radical containing from 1 to 20 carbon atom, each R$^7$ is an independently monovalent hydrocarbon radical containing from 1 to 20 carbon atoms and R$^8$ is a divalent hydrocarbon of containing 2 to 20 carbon atoms and optionally contains an oxygen atom or an —NR$^7$— group; and x is an integer from 1 to 500;

each E$^1$ is a monovalent end-group independently selected from the group consisting of, and H-L-; and each E$^2$ is a monovalent end-gimp independently selected from the group consisting of hydrogen, each m and n is independently an integer from 1 to 500 and a is an integer from 2 to 4, b is an integer from 2 to 100, wherein the method comprises reacting i) polysiloxane A, and
ii) polyalkylene oxide B, with at least one $E^1$ monovalent end-group and at least one $E^2$ monovalent end-group.

19. The method of claim 18 wherein b is an integer from 3 to 50 and x is an integer from 10 to 200.

20. The method of claim 18 wherein $R^1$ is an alkyl group having from one to four carbon atoms.

21. The method of claim 18 wherein $R^2$ is a chemical bond.

22. The method of claim 18 wherein $R^2$ is a hydrogen.

23. The method of claim 18 wherein $R^3$ is a hydrogen.

24. The method of claim 18 wherein $R^4$ is a methyl group.

25. The method of claim 18 wherein $R^5$ is a propyloxymethyl or methoxy group.

26. The method of claim 18 wherein $R^6$ is a propyl group.

27. The method of claim 18 wherein $R^7$ is an ethyl group.

28. The method of claim 18 wherein -L- is at least one selected from the group consisting of N,N-diethylaminopropylamino group and 3-Morpholinopropylamino group.

29. The method of claim 18 wherein components $E^1$ and $E^2$ are independently selected from the group consisting of —$CH_2CH(OH)(CH_2)_vCH(OH)CH_2$—, —$CH[CH_2OH](CH_2)_vCH[CH_2OH]$—, —$CH_2CH(OH)(CH_2)_vCH[CH_2OH]$—, —$(CH_2)_vOCH_2CH(OH)CH_2$—; —$(CH_2vOCH_2CH(CH_2[OH])$—, and v is an integer from 2 to 6.

30. The method of claim 18 wherein $E^1$ and $E^2$ are independently selected from the group consisting of ω-(3,4-epoxycyclohexyl)alkylene, β-(3,4-epoxycyclohexyl)ethylene, β-(3,4-epoxycyclohexyl)-β-methylethylene, and β-(3,4-epoxy-4-methylcyclohexyl)-β-methylethylene.

31. The method of claim 18 wherein —$C_aH_{2a}O$— is at least one of ethylene oxide wherein a equals 2, propylene oxide wherein a equals 3, and butylene oxide wherein a equals 4.

32. The method of claim 18 wherein the amine groups are protonated or quaternized.

33. A personal care product comprising the composition prepared from the method of claim 18.

34. A textile enhancer comprising the composition prepared from the method of claim 18.

* * * * *